(12) United States Patent
Temple

(10) Patent No.: US 8,444,591 B2
(45) Date of Patent: May 21, 2013

(54) INSUFFLATION GAS HEATER SYSTEM AND TUBING FOR USE THEREWITH

(76) Inventor: John Temple, Chelsea, MI (US)

(*) Notice: Subject to any disclaimer, the term of this patent is extended or adjusted under 35 U.S.C. 154(b) by 424 days.

(21) Appl. No.: 12/902,826

(22) Filed: Oct. 12, 2010

(65) Prior Publication Data
US 2011/0087160 A1 Apr. 14, 2011

Related U.S. Application Data

(60) Provisional application No. 61/250,144, filed on Oct. 9, 2009.

(51) Int. Cl.
A61M 37/00 (2006.01)
A61N 1/30 (2006.01)

(52) U.S. Cl.
USPC .................... 604/26; 604/21; 604/23; 604/19

(58) Field of Classification Search
USPC ..... 604/113, 26, 23, 21, 19, 114; 128/203.16, 128/203.26, 204.17
See application file for complete search history.

(56) References Cited

U.S. PATENT DOCUMENTS

| 1,572,300 | A | * | 2/1926 | Max ............................. 392/473 |
| 5,006,109 | A | | 4/1991 | Douglas et al. |
| 5,362,310 | A | * | 11/1994 | Semm ............................ 604/26 |
| 5,411,074 | A | | 5/1995 | Naruse et al. |
| 5,411,474 | A | * | 5/1995 | Ott et al. ........................ 604/26 |
| 5,439,441 | A | | 8/1995 | Grimsley et al. |
| 5,620,440 | A | * | 4/1997 | Heckele et al. ................. 606/28 |
| 6,010,118 | A | | 1/2000 | Milewicz |
| 6,068,609 | A | | 5/2000 | Ott et al. |
| 6,632,194 | B1 | * | 10/2003 | Mehner et al. ................. 604/26 |
| 6,976,489 | B2 | | 12/2005 | Mantell et al. |
| 7,006,902 | B2 | * | 2/2006 | Archer et al. ..................... 701/1 |
| 7,066,902 | B1 | | 6/2006 | Ott et al. |
| 7,250,035 | B1 | | 7/2007 | Ott et al. |
| 7,429,257 | B2 | | 9/2008 | Novak et al. |
| 7,647,925 | B2 | | 1/2010 | Mantell et al. |
| 7,744,557 | B2 | | 6/2010 | Ott et al. |
| 2003/0014004 | A1 | | 1/2003 | Dey |
| 2003/0181857 | A1 | | 9/2003 | Blake et al. |
| 2004/0102731 | A1 | * | 5/2004 | Blackhurst et al. ............. 604/26 |
| 2005/0171466 | A1 | * | 8/2005 | Diemunsch ..................... 604/26 |
| 2006/0129098 | A1 | | 6/2006 | Hart et al. |
| 2006/0184096 | A1 | | 8/2006 | Ott et al. |
| 2007/0107726 | A1 | | 5/2007 | Mantell et al. |

FOREIGN PATENT DOCUMENTS

EP 0564953 A1 10/1993

* cited by examiner

*Primary Examiner* — Kevin C Sirmons
*Assistant Examiner* — Bradley G Thomas, Jr.
(74) *Attorney, Agent, or Firm* — Gifford, Krass, Sprinkle, Anderson & Citkowski, P.C.

(57) ABSTRACT

A warming gas flows through a jacket to heat an insufflation gas flowing in a separate tube, thereby reducing cost and disposable waste. The heated warming gas may be filtered to sterilize or maintain sterility and released to atmosphere after heating the flowing insufflation gas. Alternatively the warming gas may be reheated and recirculated through the jacket, with an additional tube being used within the jacket so that the warming gas flows in both directions lengthwise. The insufflation gas may be carbon dioxide and the warming gas may be room air. The heating element and sensors may be separate from the disposable unit of a heated insufflation set, and need not be re-sterilized prior to or after use in surgery. The heat is constantly maintained, thereby eliminating "cold spots" caused by the natural cycling of the resistance heaters due to the nature of the operation being preformed on the patient.

13 Claims, 2 Drawing Sheets

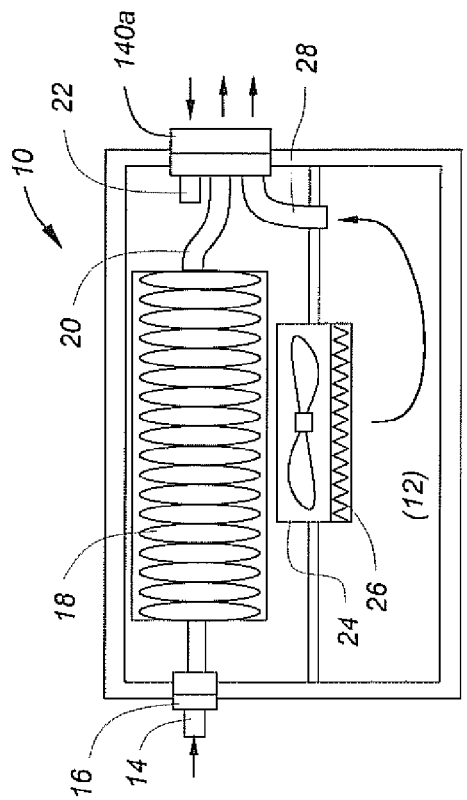
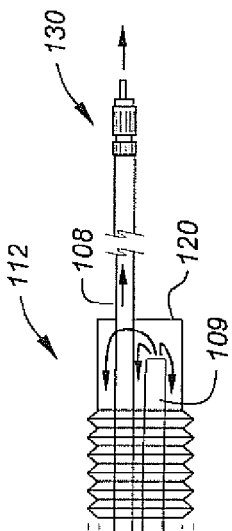
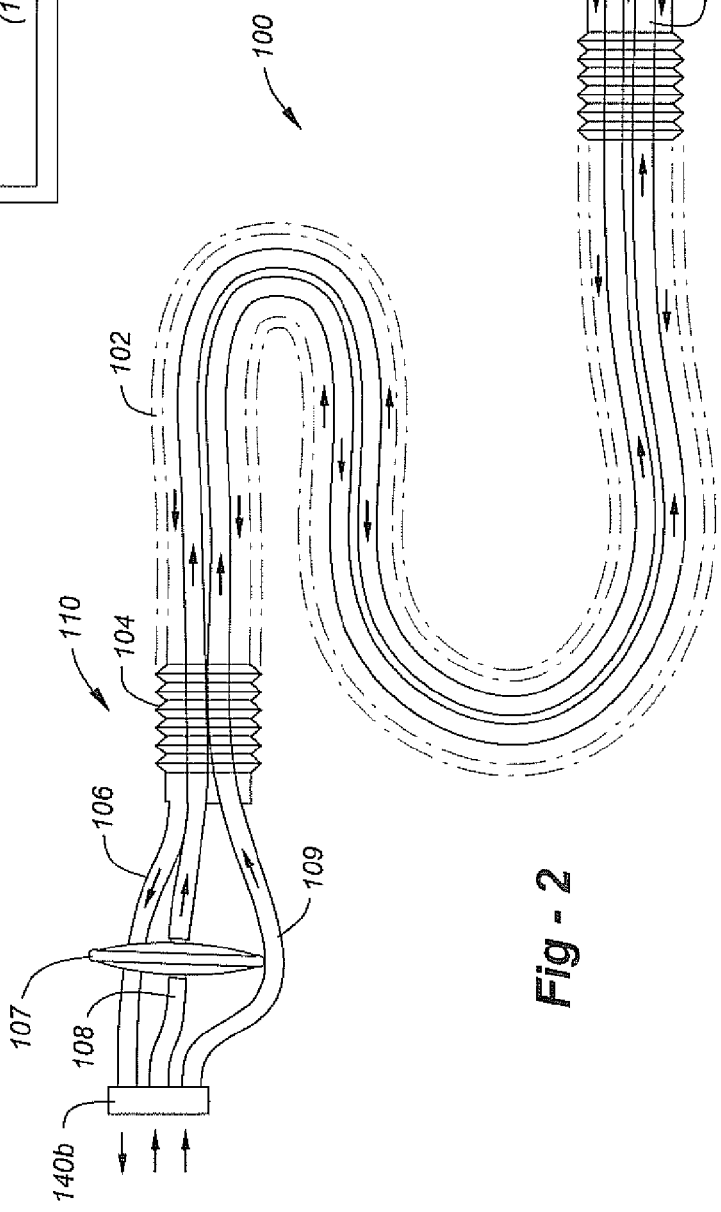
Fig - 1
Fig - 2

INSUFFLATION GAS HEATER SYSTEM AND TUBING FOR USE THEREWITH

REFERENCE TO RELATED APPLICATION

This application claims priority from U.S. Provisional Patent Application Ser. No. 61/250,144, filed Oct. 9, 2009, the entire content of which is incorporated herein by reference.

FIELD OF THE INVENTION

This invention relates generally to instruments and methods used in minimally invasive surgery and, in particular, to apparatus and methods for heating insufflation gas of the type used in laparoscopic procedures.

BACKGROUND OF THE INVENTION

Laparoscopic surgery, also called minimally invasive surgery (MIS) is a recent development in which operations in the abdominal or pelvic cavities, for example, are performed through small incisions (usually 0.5-1.5 cm) as compared to larger incisions associated with "open" surgical procedures. Laparoscopic procedures typically use images displayed on TV monitors for magnification of the surgical elements as oppose to direct visualization by the surgeon.

There are a number of advantages to the patient with laparoscopic surgery versus an open procedure. These include reduced pain due to smaller incisions and hemorrhaging, and shorter recovery time. A key element is the use of a laparoscope, which may either be a telescopic rod lens system connected to a video camera or a digital laparoscope wherein an image sensor is located at the end of the laparoscope, thereby eliminating the rod lens system. Also attached is a fiber optic cable system connected to a light source (i.e., halogen or xenon), to illuminate the operative field.

During laparoscopic surgery, the abdomen (or other cavity) is usually insufflated, or blown up like a balloon, with carbon dioxide (or other) gas. This elevates the abdominal wall above the internal organs like a dome to create a working and viewing space. $CO_2$ is used because it is common to the human body and can be absorbed by tissue and removed by the respiratory system. It is also non-flammable, which is important because electrosurgical devices are commonly used in laparoscopic procedures.

It has been suggested that replacing cold, dry $CO_2$ with heated, humidified gas for insufflation during complex laparoscopic procedures offers certain benefits, including decreased hypothermia and peritoneal cell desiccation, with a resultant decrease in postoperative pain and a shortened recovery. This has led to the development of numerous heated insufflation sets, many of which include humidification apparatus.

One commercially available insufflation gas heater uses a separate heater "box" built into the set close to the patient. The heater is controlled by a separate heat controller remote from the heater, and may therefore be situated outside the sterile field. Other types use resistance wire heaters placed inside of the tubing. These wires are usually accompanied by an over-heat fuse. Some of these sets have wires which extend the overall length of the set, while others use resistance heating limited to the patient end. In some cases the wires are coiled; in other cases the wires are straight.

There are several drawbacks to these existing approaches. The deficiencies are related to the fact that the $CO_2$ gas does not flow continuously but is instead intermittent, with flow in the range of 0 to 40 liters per minute. When first filling the body cavity the flow is very high; a high flow rate may also occurs at other points in the operation as the surgeon manipulates instruments. With the flow of cold $CO_2$, the controller delivers power to the resistance heater, and while this may occur rapidly, heat-up is limited by the need to avoid over heating which could burn the patient. Often times this results in unheated $CO_2$ entering the patient.

Also existing sets are very expensive, as the heating element in all of the sets is disposable. In products that use a heater "box," the entire heater unit either has to be to be autoclaved or thrown out and replaced with each use. The need remains for a more elegant solution.

SUMMARY OF THE INVENTION

This invention improves upon existing insufflation gas heaters through the use of a warming gas which flows through a jacket to heat an insufflation gas flowing in a separate tube, thereby reducing waste the cost of the equipment involved. Since the $CO_2$ does not flow directly over a heater such as a resistance wire as it travels from an insufflator to a patient, the heating element (and sensors) may separate from the disposable unit of a heated insufflation set, thereby reducing disposable waste. The heating element and sensors also need not be cleaned or re-sterilized prior to, or after, use in surgery, which reduces the cost of production of the disposable set and or the operation. Moreover, the heat is constantly maintained, thereby eliminating "cold spots" caused by the natural cycling of the resistance heaters due to the nature of the operation being preformed on the patient.

A basic system for heating insufflation gas in accordance with the invention comprises first and second tubes. The first tube carries insufflation gas from a proximal end to a distal end adapted for connection to an instrument used to inflate a body cavity with the insufflation gas. The second tube, surrounding or adjacent to the first tube, carries a warming gas to heat the first tube and the insufflation gas flowing therethrough. If the insufflation gas is already sufficiently warm, the system and method may be used to maintain temperature as opposed to "heating" it.

The system may include a filter for sterilizing the warming gas so that it may be released into a surgical field at the distal end after heating the first tube and insufflation gas. Alternatively, the system may include a third tube within the second tube for carrying the warming gas from the proximal end of the first tube to the distal end of the second tube where the warming gas is released to flow back toward the proximal end and around the first tube. A port at the proximal end enables the warming gas to exit the second tube so that it can be re-heated and recirculated back into the third tube.

The system may include one or two heaters, depending upon the configuration, as described herein in detail.

BRIEF DESCRIPTION OF THE DRAWINGS

FIG. 1 is a schematic diagram of a device to heat insufflation gas constructed in accordance with the invention.

FIG. 2 depicts a tubing assembly for use with the heater of FIG. 1;

DETAILED DESCRIPTION OF THE INVENTION

Figure 3:
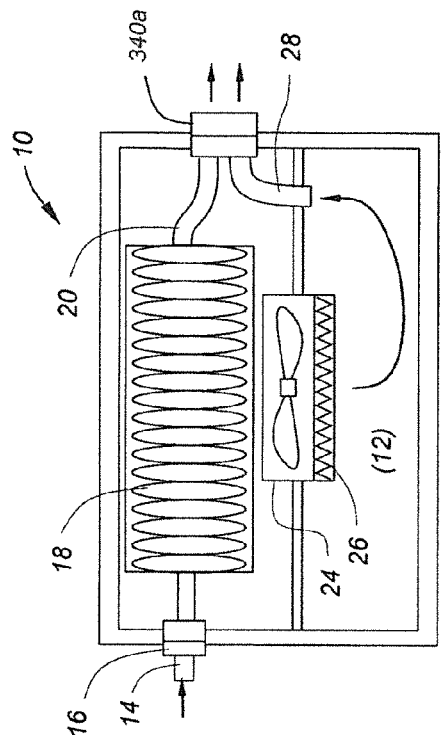
FIG. 3 depicts an alternative heater.

This invention relates to instruments and methods used in minimally invasive surgery (MIS) and, in particular, to apparatus and methods using a warming gas for heating insufflation gas of the type used in laparoscopic procedures. In all preferred embodiments, the insufflation gas is carbon dioxide and warming gas is air.

One embodiment of the invention uses two remote heaters; one to heat the $CO_2$ insufflation gas to body temperature prior to entering the patient, and a second heater to control a circular flow of warming gas (i.e., room air) in a jacketed tubing assembly to heat the insufflation gas. The heaters may both run at a constant temperature of approximately 98° F. (i.e., 98±7°). As such, heat entering the body will be approximately 98° because the $CO_2$ has been preheated and heat is not allowed to escape into the atmosphere though the tubing walls.

As an alternative to a separate heater for the insufflation gas, a single heater for the warming gas may be provided if the temperature and/or flow rate are sufficient. As a further alternative, a single heater may be used for the warming gas with the insufflation gas passing through a heat exchanger to prewarm the insufflation gas prior to entry into the jacketed tubing assembly.

As described in further detail herein below, the jacketed tubing assembly may have one or two internal tubes, depending upon whether the warming gas is recirculated or released in to the environment. If the warming gas is recycled (and re-heated), it need not be sterile as it does not enter the sterile surgical field. If the warming air is released after use, it preferably passes through a filter to "sterilize" the air, (i.e., to remove bacteria or virus). This latter configuration has the advantage of requiring only two tubing layers. This approach is less costly, easier to manufacture, and the tubing set is lighter and more flexible which may be desired in the marketplace. A dispersing member may be used to diffuse the preheated gas as it exits the tubing.

Referring to the Figures, a system according to one embodiment of the invention includes a heater unit depicted generally at 10 and a tubing assembly shown generally at 100. The length of the tubing assembly is variable, but may be on the order of 10 feet, or thereabouts. It should be understood that these drawings are intended to illustrate important structural components and operational functionality and are not necessarily drawn to scale.

The tubing assembly 100 attaches to the heater unit 10 by way of a connector 140a, 140b as described in further detail with respect to FIG. 2. Insufflation gas such as carbon dioxide enters the heater unit 10 through port 14. The gas is carried by an appropriate conduit coupled to a source of pressure-controlled insufflation gas (not shown) at a rate typically in the range of 0.5-30 liters/min. The insufflation gas passes through coupling 16 and into heater unit 18 which heats the gas. Heater unit 18 may be a Cast-X type heater from Watlow of St. Louis, Mo., a self-contained unit using medical grade stainless-steel tubing. The heated insufflation gas passes through tube 20 and exits the heater via coupling 140a. All components are sterilized such that the sterility of the insufflation gas is maintained throughout.

Air or other warming gas is delivered by fan 24 and heated by heater 26 which may be a Model 375 finned strip heater, also available from Watlow. The warming gas is routed to tube 28 and through coupling 140a to the tubing assembly 100 at a flow rate in correlation to the heater temperature, which could be in the range of 1-2 cfm, enabling a desired heat to be maintained within the tube, depending upon the length of the tubing assembly and other factors. Return warming gas is received from inlet 22 through coupling 140a, which is recycled through fan 24 and reheated by heater 26 due to partition 12 in the heater unit 10.

Turning now to FIG. 2, as mentioned coupling 140b attaches to coupling 140a, thereby connecting tube 106 to tube 22; tube 108 to tube 20; and tube 109 to tube 28. Tube 108 carrying warmed $CO_2$ may pass through filter 107. The warming gas travels through tube 109 from the proximal end 110 of the assembly to the distal end 112, at which point it emerges into outer tube 102, which may include lengthwise accordion structure 104. As the warming gas travels back through the outer tube it heats or maintains the temperature of the $CO_2$ in tube 108, which may terminate in a standard Luer-Lok fitting 130 for interconnection to an instrument used for body cavity inflation.

In operation, the temperature of the gas used for insufflation may be maintained at a desired temperature, as in the range of 100° F. As such, the temperature of the warming gas may be set somewhat high to account for loss to the ambient environment. Although not shown, various temperature sensors and/or feedback systems may be incorporated to ensure reliable operation. For example, one or thermistors may be included to monitor the temperature of either or both heaters or the gasses directly to maintain temperature control or to terminate heating if it becomes excessive.

All of the tubes depicted in FIG. 2 may be made of flexible plastic material. A distinct advantage of the system is that the tubing assembly 100 maintains temperature of the insufflation gas without the need for electrical heaters integral to the tubing, thereby reducing the cost of the tubing assembly 100, which is typically discarded and replaced following each procedure. Although separate tubes are shown for the insufflation gas and warming gas, in alternative embodiments an extrusion process may be used to form three or more tubes simultaneously so that they touch or are at least in close proximity.

In the embodiment of FIGS. 1, 2 the warming gas is recycled and not released into the ambient atmosphere of the surgical suite. This has two advantages: one, the warming gas need not be sterile (through filtration may be added for such purpose), as the system is closed-loop; and two, the previously heated warming gas is essentially re-heated, which may cut down on power requirements. A disadvantage, however, is that the tubing assembly 100 required three passageways—one for the insufflation gas and two for the warming gas The embodiment of FIGS. 3, 4 uses an additional filter 411 to ensure that the warming gas is sterile, enabling the gas to be released through port 412 at the distal end 420 of the tubing assembly. Although the warming gas filter is shown at the proximal end of the tubing assembly, it may alternatively be positioned inside the heater unit 10 or at the distal end 420 immediately prior to the exit port 412.

Figure 4:
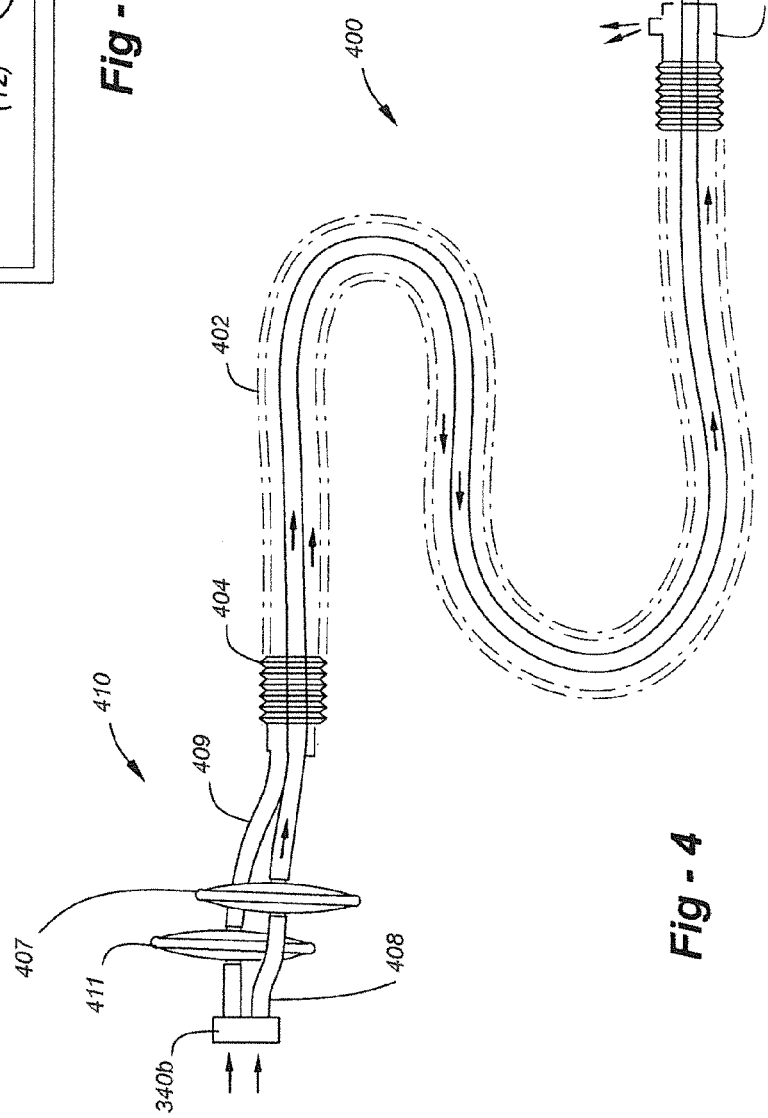
FIG. 4 is a drawing that shows an alternative tubing assembly which eliminates a return heated gas line.

Otherwise the system and method of FIG. 3, 4 is similar to those described with reference to FIGS. 1, 2. The tubing assembly 400 connects to the heater unit 10 through connector 340a, which now only has two passageways. Connector 340a connects to 340b, coupled to hoses 408, 409, which are filters by filters 407, 411, respectively. Tube 402, containing only one inner conduit 408 (which terminates at connector 430), may be smaller in diameter and less expensive. As with tube 102, tube 402 may include an accordion structure shown schematically at 404.

As discussed earlier, if the temperature and/or flow rate of the warming gas is sufficient, a separate heater for the insufflation gas (i.e., heater unit 18 in FIGS. 1 and 3) may be eliminated. As a further alternative, the insufflation gas may pass through a heat exchanger associated with heating the warming gas (i.e., heater 26 in FIGS. 1 and 3) prior to entry into the tubing assemblies shown in FIGS. 2, 4.

I claim:

1. A system for heating or maintaining the temperature of an insufflation gas, comprising:
   a first tube for carrying insufflation gas from a proximal end to a distal end adapted for connection to an instrument used to inflate a body cavity with the insufflation gas; and
   a second tube surrounding or adjacent to the first tube, the second tube carrying a warming gas to heat or maintain the temperature of the first tube and the insufflation gas flowing there through;
   wherein the first tube is impermeable to the warming gas to maintain sterility of the insufflation gas in the first tube.

2. The system of claim 1, wherein:
   the second tube surrounds the first tube; and
   further including a third tube within the second tube for carrying the warming gas from the proximal end of the first tube to the distal end of the second tube where the warming gas is released to flow back toward the proximal end and around the first tube.

3. The system of claim 1, wherein:
   the second tube surrounds the first tube;
   a third tube within the second tube for carrying the warming gas from the proximal end of the first tube to the distal end of the second tube where the warming gas is released to flow back toward the proximal end and around the first tube; and
   a port at the proximal end enabling the warming gas to exit the second tube and be re-heated and returned to the third tube.

4. The system of claim 1, wherein:
   the second tube surrounds the first tube; and
   further including a filter for sterilizing the warming gas so that it may be released into a surgical field at the distal end after heating the first tube and insufflation gas.

5. The system of claim 1, further including a heater for heating the insufflation gas.

6. The system of claim 1, further including a heater for heating the warming gas.

7. The system of claim 1, wherein the insufflation gas is carbon dioxide.

8. The system of claim 1, wherein the warming gas is air.

9. A system for heating insufflation gas, comprising: a heater for heating a warming gas; a first tube for carrying insufflation gas from a proximal end adapted for connection to a source of insufflation gas to a distal end adapted for connection to an instrument used to inflate a body cavity with the insufflation gas; and a second tube having proximal and distal ends forming a co-extensive jacket around the first tube, the second tube receiving heated warming gas to heat the first tube and the insufflation gas flowing there through; wherein the first tube is impermeable to the warming gas to maintain sterility of the insufflation gas in the first tube.

10. The system of claim 9, wherein the heated warming gas is introduced at the proximal end of the second tube and release into the ambient environment at the distal end of the second tube.

11. The system of claim 10, further including a filter to filter the warming gas prior to being released into the ambient environment.

12. The system of claim 9, further including:
    a port at the proximal end of the second tube;
    a third tube within the second tube, the third tube having an open distal end terminating prior to the distal end of the second tube; and
    wherein the warming gas is introduced into the third tube and expelled at the distal end thereof to flow back and around the first tube and out the port to be re-heated and recirculated.

13. The system of claim 9, further including a heater for heating the insufflation gas prior to entry into the first tube.

* * * * *